(12) United States Patent
Tihon

(10) Patent No.: US 10,219,808 B2
(45) Date of Patent: Mar. 5, 2019

(54) PARTIAL CUFF

(71) Applicant: Claude Tihon, Eden Prairie, MN (US)

(72) Inventor: Claude Tihon, Eden Prairie, MN (US)

( * ) Notice: Subject to any disclaimer, the term of this patent is extended or adjusted under 35 U.S.C. 154(b) by 203 days.

(21) Appl. No.: 15/259,799

(22) Filed: Sep. 8, 2016

(65) Prior Publication Data

US 2016/0374686 A1 Dec. 29, 2016

Related U.S. Application Data

(63) Continuation-in-part of application No. 12/122,079, filed on May 16, 2008, now Pat. No. 9,956,067.

(60) Provisional application No. 60/958,420, filed on Jul. 6, 2007, provisional application No. 61/011,750, filed on Jan. 22, 2008.

(51) Int. Cl.

| | | |
|---|---|---|
| *A61B 17/132* | (2006.01) | |
| *A61F 2/00* | (2006.01) | |
| *A61B 17/28* | (2006.01) | |
| *A61B 17/135* | (2006.01) | |
| *A61B 17/00* | (2006.01) | |
| *A61F 2/06* | (2013.01) | |
| *A61B 17/12* | (2006.01) | |
| *A61F 2/04* | (2013.01) | |
| *A61F 2/30* | (2006.01) | |

(52) U.S. Cl.
CPC ........ *A61B 17/1325* (2013.01); *A61B 17/135* (2013.01); *A61B 17/282* (2013.01); *A61F 2/004* (2013.01); *A61F 2/0036* (2013.01); *A61B 17/12* (2013.01); *A61B 17/1355* (2013.01); *A61B 2017/00805* (2013.01); *A61F 2/0063* (2013.01); *A61F 2/06* (2013.01); *A61F 2002/044* (2013.01); *A61F 2002/30077* (2013.01); *A61F 2210/0066* (2013.01)

(58) Field of Classification Search
CPC ... A61B 17/12; A61B 17/1325; A61B 17/135; A61B 2017/00805; A61F 2002/044; A61F 2/0036; A61F 2/004; A61F 2/0063
See application file for complete search history.

(56) References Cited

U.S. PATENT DOCUMENTS

| | | |
|---|---|---|
| 3,726,279 A | 4/1973 | Barefoot et al. |
| 3,863,622 A | 2/1975 | Buuck |
| 4,222,377 A | 9/1980 | Burton |
| 4,428,365 A | 1/1984 | Hakky |

(Continued)

FOREIGN PATENT DOCUMENTS

FR 2 373 272 A1 7/1978

*Primary Examiner* — Christine H Matthews
(74) *Attorney, Agent, or Firm* — Crawford Maunu PLLC

(57) ABSTRACT

Aspects of the present disclosure are directed toward providing enhanced structural support to an organ. As may be implemented in accordance with one or more embodiments, an apparatus includes structure configured and arranged to partially encircle a tubular organ, having a semi-cylindrical shape with a tapered end and blunt end of the cylinder. A gap region provides a region of the organ that is unrestricted/unsupported. Struts/lattice facilitate ingrowth of tissue, and couple the apparatus to the organ, which allows the apparatus to provide support/restrict flow in the organ without necessarily coupling to any other structure (e.g., with the majority or all of the support provided via the apparatus as coupled onto and terminating on a sidewall of the tubular organ).

19 Claims, 13 Drawing Sheets

(56) References Cited

U.S. PATENT DOCUMENTS

| | | | |
|---|---|---|---|
| 4,634,443 | A | 1/1987 | Haber |
| 4,909,785 | A | 3/1990 | Burton et al. |
| 4,994,020 | A | 2/1991 | Polyak |
| 5,948,191 | A | 9/1999 | Solovay |
| 6,432,040 | B1 | 8/2002 | Meah |
| 6,491,623 | B2 | 12/2002 | Snyder et al. |
| 6,491,703 | B1 | 12/2002 | Ulmsten |
| 6,612,977 | B2 | 9/2003 | Staskin et al. |
| 7,083,637 | B1 | 8/2006 | Tannhauser |
| 2005/0055104 | A1 | 3/2005 | Arnal et al. |
| 2005/0288596 | A1 | 12/2005 | Eigler et al. |
| 2005/0288776 | A1 | 12/2005 | Shaoullan |
| 2006/0129027 | A1 | 6/2006 | Catona |
| 2007/0049790 | A1 | 3/2007 | Wagner et al. |
| 2007/0156158 | A1* | 7/2007 | Herzberg ........... A61B 17/1146 606/152 |
| 2007/0276342 | A1 | 11/2007 | Lin et al. |

\* cited by examiner

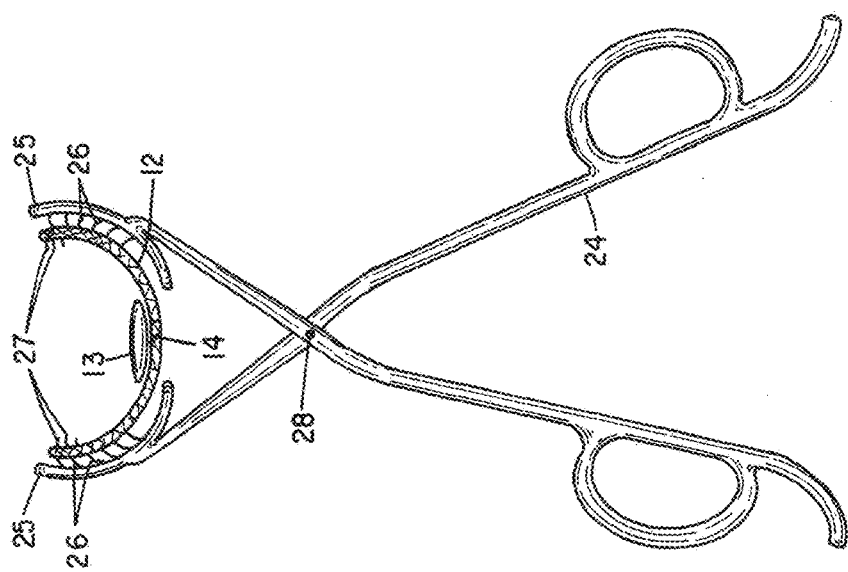
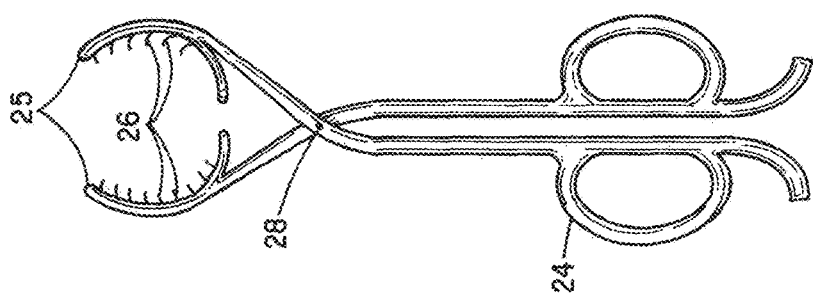
FIG. 8b
FIG. 8a

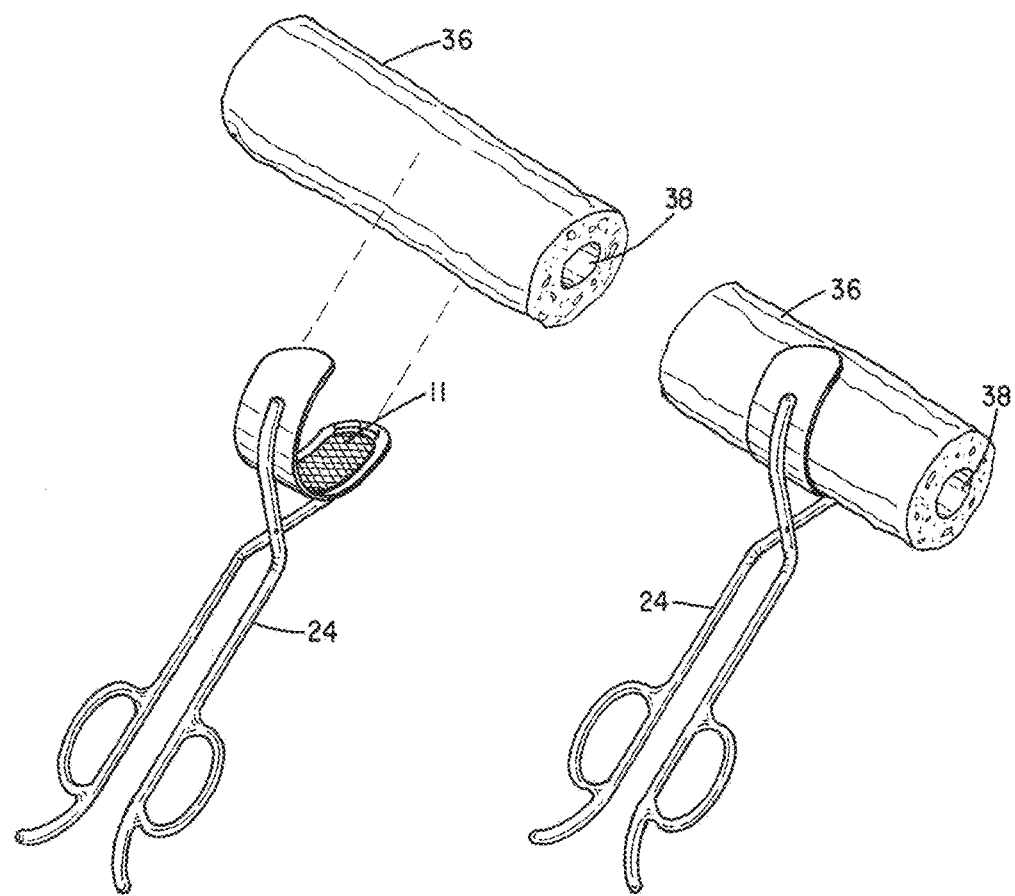
FIG. 8c
FIG. 8d
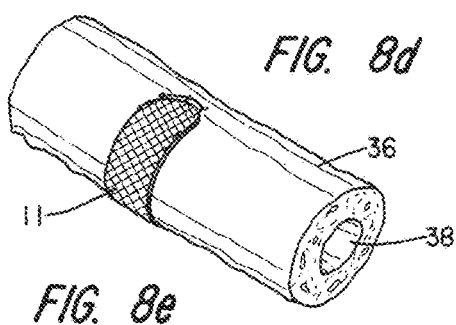
FIG. 8e

PARTIAL CUFF

FIELD

Aspects of various embodiments are directed to flow modulation and/or restriction, and to a cuff that is attachable directly to a tubular organ for increasing the flow resistance of liquids and substances through the tubular organ.

BACKGROUND

Biological tubular organs in our body are conduits for fluids, food and wastes. For example, the urethra is the conduit for urine between the bladder and the urethral meatus and it also functions to inhibit involuntary leakage. In stress urinary incontinence, urine may leak involuntarily when a person coughs or laughs, or under other conditions. Stress urinary incontinence can be managed by absorbents and surgical interventions.

While various approaches to treating urinary incontinence have been implemented, such approaches have been challenging. For example, implanting medical devices can have undesirable effects. One such issue may involve puncturing the bladder and/or blood vessels, and other damage to the bladder, blood vessels, nerves and muscles. These issues may be exasperated in women patients who have future child births. Another issue relates to the coupling of an implanted medical device to anatomical structures in addition to the organ being treated for incontinence, which can cause damage and further be difficult to implement with a desired/controlled result. For instance, relying upon coupling to other such anatomical structures for controlling flow through a tubular organ may result in inaccurate control relative to one or more of variations in the other anatomical structures from patient to patient, and to changes in the other anatomical structures over time after implantation.

These and other matters have presented challenges to flow control, for a variety of applications such as those involving biological tissue and flow therein.

SUMMARY

Various example embodiments are directed to flow restriction in organs, and to cuffs used to control flow in tubular organs, their manufacture and their implementation.

According to an example embodiment, an apparatus includes a perimeter structure and a plurality of struts extending between respective portions of the perimeter structure, with spaces between the struts that facilitate ingrowth and/or fibrosis of tissue. The perimeter structure has a semi-cylindrical shape extending contiguously from a first end to a second end along a circumference thereof. A gap region between the first and second ends and along the circumference provides an open side of the semi-cylindrical shape, and facilitates coupling of the apparatus to a tubular organ. In this context, the gap may be applied to partially encircle a tubular organ, with an outer surface of the tubular organ growing between the struts. The tubular organ is allowed to expand readily at the gap region where the organ is unconstrained, while the portion of the apparatus in contact with the tubular organ mitigates expansion thereof. The semi-cylindrical shape has a tapered edge and a blunt edge at opposing ends of the perimeter structure, and along the axis of the semi-cylindrical shape. The tapered edge has a length along the circumference that is less than a length along the circumference at the blunt edge, such that passage of material through the tubular organ from the tapered edge is facilitated. The struts mitigate expansion of a sidewall of the tubular organ to which the struts are coupled while allowing expansion of another portion of the tubular organ between the first and second ends along the circumference.

Various embodiments are directed to a surgical device and method to restrict flow, such as to treat urinary incontinence, utilizing a cuff with a flexible base member that partially surrounds a tubular structure such as the urethra. In such applications, the partial cuff does not occlude the urethra. The cuff may, but need not, incorporate an adjustable, expandable or deflatable component that applies pressure on one side of the urethra, allowing accurate adjustment to achieve desired coaptation while allowing the patient to void naturally and normally. The cuff may be used with various biological tubular organs such as the ureter, anal sphincter, stomach, esophagus, and heart. Hence, various conditions where a flow of material needs to be modulated in a biological tube can be treated.

Certain embodiments involve a simple, minimally invasive surgical procedure. Adjustments can be made after surgery and after tissues have healed by providing positive pressure to achieve a desired amount of coaptation needed by the patient's condition. Natural and volitional voiding can be achieved for incontinent patients.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which:

FIG. 1b is a side elevation of the embodiment of FIG. 1a;
FIG. 3b is a side elevation of the embodiment of FIG. 3a;
FIGS. 8a through 8e illustrate the manner in which a specially designed tool can be used to secure a cuff to the exterior wall of a tubular organ.

FIGS. 17a-17f show respective views of a latticed structure, in accordance with another embodiment, in which:

FIG. 17a shows a front view;

FIG. 17b shows a side view;

FIG. 17c shows a perspective view;

FIG. 17d shows a top view;

FIG. 17e shows a section view; and

FIG. 17f shows another section view; and

Figure 1A:
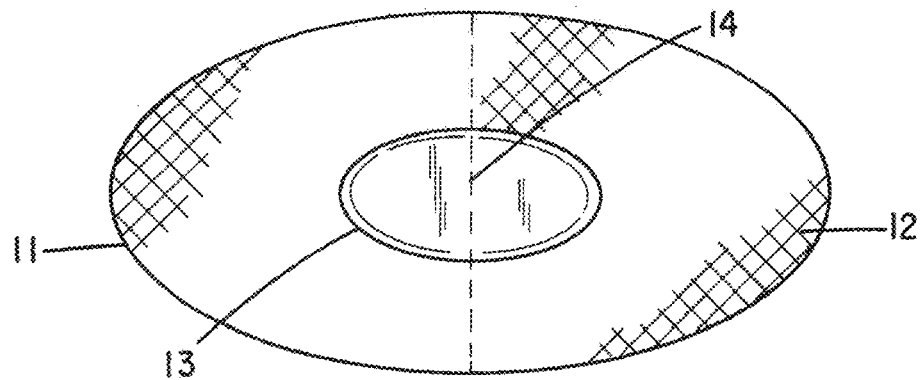
FIG. 1a is a top plan view of a first embodiment.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving a partial cuff apparatus, its manufacture and/or implementation involving the control of fluid flow. In certain implementations, aspects of the present disclosure have been shown to be beneficial when used in the context of controlling incontinence in human urethra, or with control of fluid flow in other tubular organs such as the esophagus, stomach, colon, blood vessels and heart. Various such aspects employ a partial cuff with sufficient rigidity to restrict the fluid flow without necessarily utilizing any coupling to other anatomical structures, such as by using rigidity of the cuff itself along with its attachment to the tubular organ to independently provide the increased stiffness. While not necessarily so limited, various aspects may be appreciated through a discussion of examples using such exemplary contexts.

In accordance with a particular embodiment, an apparatus includes a perimeter structure and a plurality of struts extending between respective portions of the perimeter structure, with spaces between the struts that facilitate ingrowth and/or fibrosis of tissue. The perimeter structure exhibits a semi-cylindrical shape extending contiguously from a first end to a second end along a circumference thereof, with a gap between the first and second ends along the circumference. In this context, the gap may be applied to partially encircle a tubular organ, with an outer surface of the tubular organ growing between the struts. The semi-cylindrical shape has a tapered edge and a blunt edge at opposing ends of the perimeter structure, and along the axis of the semi-cylindrical shape. The tapered edge has a length along the circumference that is less than a length along the circumference at the blunt edge, such that passage of material through the tubular organ from the tapered edge is facilitated. The struts mitigate expansion of a sidewall of the tubular organ to which the struts are coupled while allowing expansion of another portion of the tubular organ between the first and second ends along the circumference.

Rigidity as characterized herein and related to the flow of material through a structure, involves the type, thickness and structural arrangement of material. For instance, a sloped edge may create a differential containment of a biological tubular wall. As expansion of the tubular wall is mitigated by contact with the wall, a non-constrained biological wall portion is free to expand as physiology dictates. For instance, a non-constrained esophagus wall within a device zone is able to expand more than a region where there is more wrap of the device, creating a wedge effect. In the reverse direction, an abrupt constraint is provided (no slope/taper) and, together with the fact that the wall muscles are not relaxed in that situation, reverse flow is inhibited.

According to various example embodiments, aspects of the present disclosure are directed to a cuff that partially surrounds an anatomical tubular organ, such as the urethra. Many biological soft tissue tubes are expandable in girth to accommodate passage of material through their lumen. The muscle components in the wall of the tube provide tonicity and elasticity. For example, the stomach expands as food enters, the esophagus opens up to allow food to pass down, the lower esophageal sphincter or the cardiac sphincter opens to allow passage of food but closes to prevent regurgitation of food material and stomach acid up the esophagus, intestines expand to accommodate food material and provides peristaltic action to propagate the food material down its length, and the urethra expands to allow urine to flow through. After the material has exited, the diameter of the tubular organ again retracts to its non-expanded size. The attachment of a partial cuff, made of non-elastic or limited elasticity material, and that partially surrounds the tubular organ, limits the expansion of the portion of the tubular organ covered by the cuff, allowing the non-covered portion to expand. For material to pass through this juncture with the reduced expandable wall tissue, a higher force is required to open the passage way. The reduced amount of expandable tissue at the site of the partial cuff results in a higher tissue tension that would require a higher force in order to push the same amount of material through this juncture. The lesser amount of tissue allowed to expand results in either a higher pressure to open the lumen to the same size or allowing only a smaller lumen to be opened due to limits on tissue stretch, or both. The partial cuff induces an increased tonicity to the biological tubular organ, providing increased material passage resistance in a biological soft tissue tube while still maintaining the profile of the biological tube.

In various embodiments, a partial cuff is used to treat stress urinary incontinence, by adding reinforcement to maintain the urethral closure pressure while not occluding the urethra. Such a partial cuff can improve continence and allow patients to void naturally and volitionally. This augmentation of a higher urethral tonicity for closure means an increased resistance to urine flow in stress situations such as when the patient laughs and coughs. As the cuff becomes an integral portion of and moves with the urethra, its ability to provide continence is not affected by the physical position the patient happens to be in or gravity. Because the partial cuff can be attached to the urethra without being tied to another anatomical structure such as tissue or bone, challenges such as those characterized in the background above can be addressed. As the partial cuff may be applied to urinary tract anatomy without coupling to or otherwise involving other anatomical structures, urological surgeons implanting such a partial cuff may generally have intimate knowledge of the operating field, and surgical implantation can be carried out without implementing long rods passing through various anatomical structures.

Various embodiments are directed to a partial cuff having a shape that facilitates passage of material through a biological structure in a first direction, and that mitigates or hinders passage of material in a second direction, such as in a reverse flow direction. For instance, a partial cuff may be provided with a relatively high resistance to deformation of the cuff necessary to provide reverse flow, with a relatively lower resistance to deformation of the cuff that is necessary to provide a desired direction of flow.

Some embodiments involving directional flow control are implemented to treat acid reflux type situations. In acid reflux or gastroesophageal reflux disease (GERD), acidic stomach contents reflux into the esophagus causing burning and discomfort to the sufferer. Over time, erosion of the esophageal lining occurs and could cause a condition known as Barrett's Esophagus which increases the chances of it becoming esophageal cancer. These aspects can be mitigated and/or prevented using a partial cuff in this regard.

In a particular application, a cuff is provided with sloped leading edges that allow a biological tube-type structure to which the cuff is attached to exhibit relatively low constraint, and provides a relatively larger opening. This larger opening facilitates passage of material through the biological tube-type structure beginning at the opening region adjacent the sloped leading edges. A trailing edge of the cuff provides a more blunt structure that provides stronger resistance to expansion due to material in the biological tube-type structure. The angle and length of the sloped edges can be varied to vary the wedge effect of the device in allowing material pass-through. A steeper angle with a longer slope will allow more wedge effect, and less constraint. As such, various embodiments involve setting/tuning such aspects to suit a desired resistance to flow.

Various embodiments involve GERD conditions in which food bolus coursing down an esophagus via peristaltic action of the esophagus expands the esophagus diameter, with such expansion facilitated via the sloped leading edges. The food bolus entering the device zone may thus form a wedge shaped esophageal tube enlargement. This wedge effect facilitates opening/deformation of the cuff and allows passage of the food bolus. For the reverse direction, such as when acidic stomach content is being forced upward into the esophagus, blunt ends of the cuff provide a greater resistance to expansion. For instance, absent the sloped shape, food or other material flowing in a reverse-flow direction faces the blunt ends of cuff, which may result in no wedge effect as noted above. The full force of the cuff is thus imparted on the reverse flow, which can be useful (as an example) to hinder acid reflux. In effect, a wrap angle greater than 180 degrees can create a device lateral opening that is smaller than the diameter of the device, whereas sloped edges facilitate a larger device opening (facing the slope).

In various embodiments, a sloped opening to a partial cuff is implemented to facilitate placement onto the biological tube. For instance, where a biological tube has a diameter equal to the diameter of the cuff, attaching the cuff is facilitated by using the sloped end to provide a relatively larger space in which the tube may be placed. This approach can simplify and facilitate surgical implantation of the cuff onto the biological tube.

Accordingly, as characterized above, various embodiments involve a tapered cuff, which can be implemented to facilitate application and/or directional flow control. Further such embodiments, to which the above may be applied as well, are characterized in FIGS. 16a-16c, as also discussed further below.

Figure 1B:
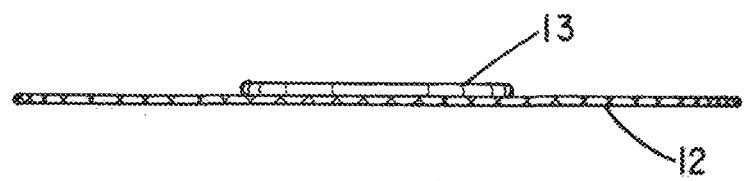

Referring to FIGS. 1a and 1b of the drawings, the partial cuff 11, comprising a first embodiment, is seen to include a flexible base member 12 that may include a latticed structure or parallel struts, which can be bio-compatible and accommodate tissue ingrowth through the interstices of the mesh material. Without limitation, the base member 12 may be generally oval or elongated in shape having a major axis measuring about 3 cms and a minor axis of about 1-112 cms when the device is to be used in addressing female urinary incontinence.

In accordance with a first aspect, there is affixed to the flexible, base member 12 an expandable component 13 having a predetermined shape configuration and generally centrally disposed on one major surface of the flexible base member 12. The expandable component 13 may comprise an elastomeric balloon capable of being inflated and deflated by an isotonic inflation fluid injected and removed through a suitable injection port. Such inflation or deflation can be manual or with an electronic control system linked to other physiological aspects.

Figure 2:
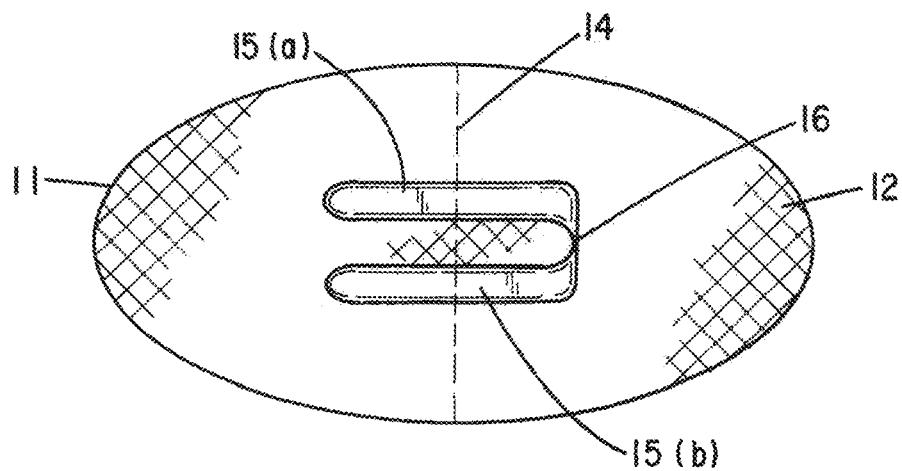
FIG. 2 is a top plan view of an alternative embodiment.

As shown in FIG. 2, the expandable component may comprise a pair of closely spaced balloon segments 15a and 15b joined together by a tubular pathway 16. When inflated, the expandable component forms a pair of ridges that are made to press upon the urethra for increasing the flow resistance thereof.

Figure 15:
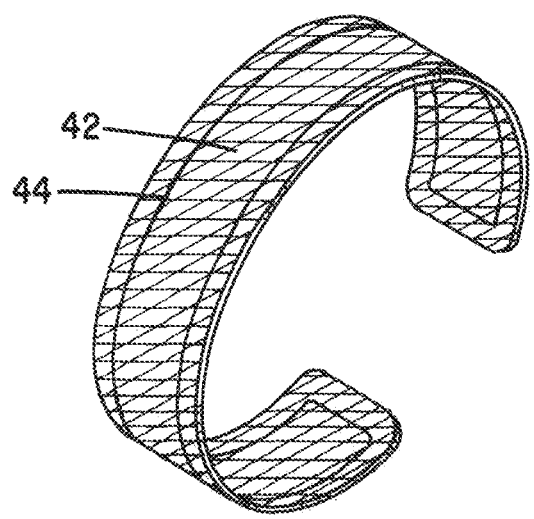
FIG. 15 shows a mesh material affixed to a C-shaped wire frame.

The expandable components 13 in FIG. 1a and 15 in FIG. 2 have their length dimension generally perpendicular to a guide line 14 that is visible to a surgeon and that is useful in appropriately aligning the cuff with respect to the patient's urethra.

Figure 3A:
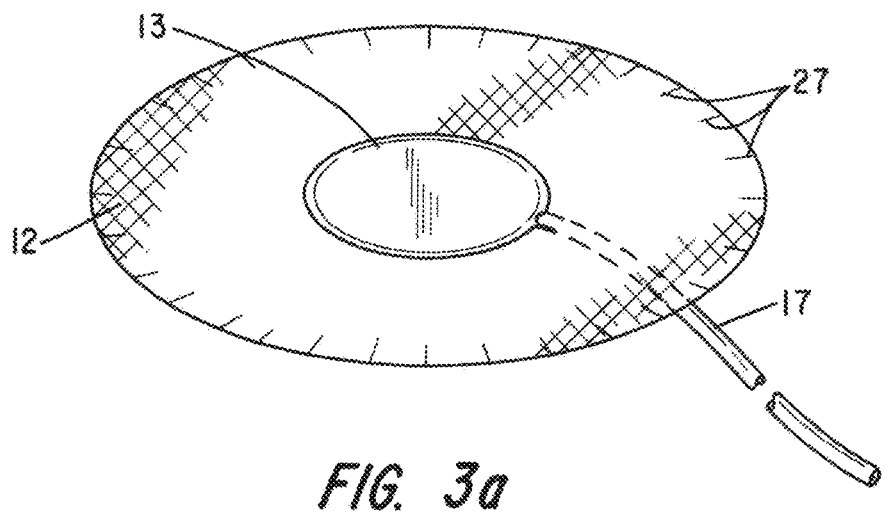
FIG. 3a shows an embodiment like that of FIG. 1 but with an inflation port feature added to it.
Figure 3B:
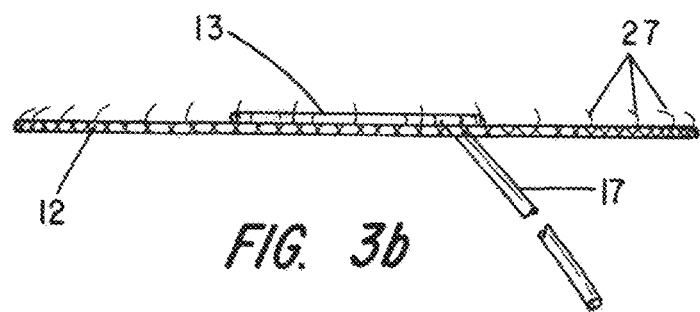
Figure 4:
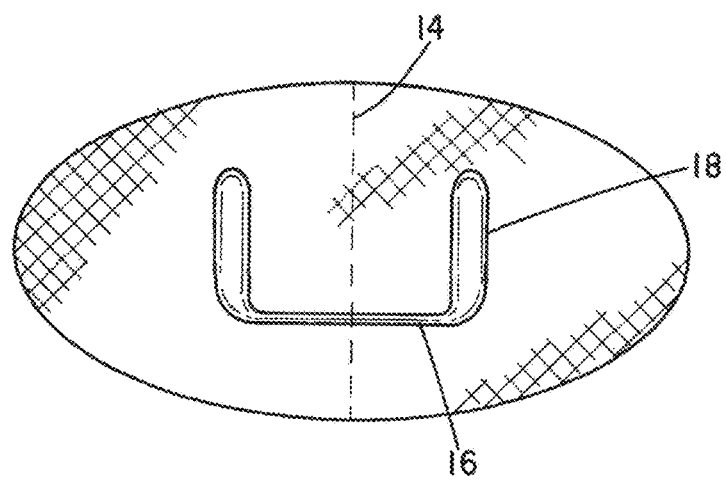
FIG. 4 is a top plan view of a further embodiment.

Turning next to FIG. 3a, it illustrates an inflation/deflation port 17 leading to the interior of the expandable component 13. In FIGS. 3a and 3b, the inflation port is illustrated as comprising a tube 17 that includes a purse-string suture thereabout (or a one-way valve or a self-sealing end) that can be used to seal the tube 17 once an inflation fluid, such as saline, has been fed through it to inflate the expandable component 13 to a desired state to thereby maintain the expandable component in its inflated condition.

Rather than utilizing a tube 17 as the inflation port, it is also contemplated that the expandable component 13 include a pad area of a self-sealing elastomeric material that is adapted to be punctured by a hypodermic needle affixed to an inflation syringe. The material of the inflation port is such that when the needle is removed, the opening self-seals to preclude leaking out of the inflation fluid.

An alternative method for adjusting the pressure applied is to deflate the balloon(s) that has been pre-inflated with saline prior to implantation. Once the structure is fully fibrosed or otherwise integrated with the tissue, the patient will come into the clinic for this post-surgical adjustment. In this case, the physician will let out a certain amount of saline (by puncturing the balloon's inflation port with a needle) till a desired level of compression is achieved. If there are separate balloons, then the deflation process is dependent on the judgment of the physician, as he may let the saline out totally in one balloon and observe its effect. If more relief is needed, he can partially empty another balloon. The endpoint will be determined with clinical observation regarding whether the patient can void without difficulties and does not leak during Valsalva's maneuver, coughing, etc. Deflation is deemed necessary when the patient is obstructed, which means he or she has difficulty voiding. Deflating the balloon or balloons will decrease the compression on the urethra, hence the urethral lumen opening, to allow urine to pass through during natural voiding.

Yet another manner to impose added pressure is by the deformation of the base member such that the convex curvature at the vertex of the arc is more linear or concaved. The degree of added compression is determined by the change in curvature away from the generally round curvature of the device. Representative embodiments are characterized in the figures.

Another possible method of pos-surgical adjustment is via heat, such as that induced by RF energy. From the weave of latticed material, the material from which it is formed or a special material integrated with the latticed material, at least a portion thereof can be made to shrink due to the externally applied heat, thus making the cuff tighter on the urethra. Again, this can be done in stages for fine tuning the effect once tissue ingrowth and fibrosis into the base member has occurred.

Also seen in FIG. 3b is a plurality of tissue piercing hooks 27 that is affixed to the base member 12 surrounding its periphery. When the partial cuff of the present invention is applied to a tubular organ, such as a subject's urethra, in a manner hereinafter described, the hooks are adapted to penetrate into the wall of the urethra and thereby hold the cuff in partial surrounding relation to the exterior urethral wall as shown in FIGS. 5 through 7 of the drawings.

The hooks 27 can be formed from a biodegradable material that will adhere the cuff to the outer wall of the urethra for a time sufficient to permit tissue ingrowth in the base member. In some embodiments, sutures are used to attach the base member to a biological structure. Such sutures can be made of bioresorbable materials.

Figure 5A:
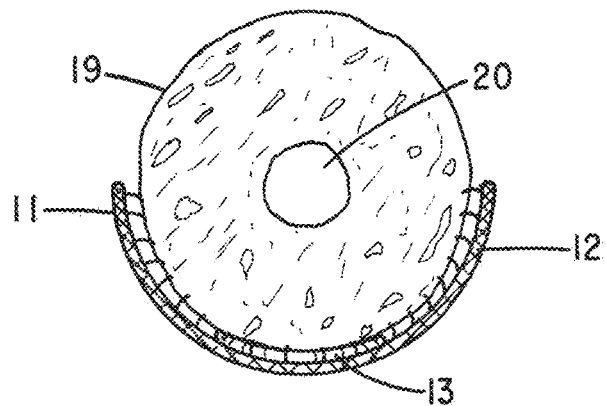
FIG. 5a is a cross-sectional view showing an embodiment coapted to a tubular organ and with the inflatable component deflated.
Figure 6A:
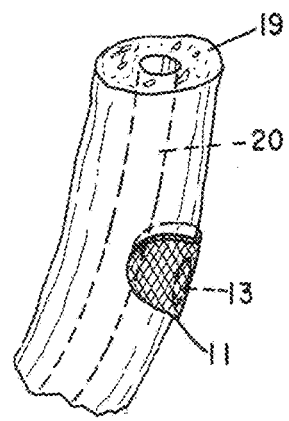
FIG. 6a is a perspective view of the cuff affixed to a tubular organ with its expandable component deflated.
Figure 6B:
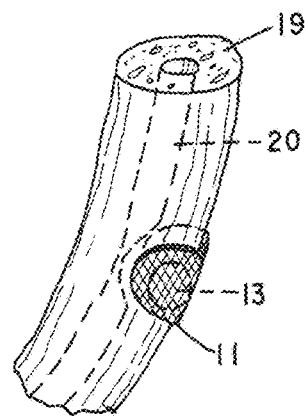
FIG. 6b is a view like that of FIG. 6a but with the expandable component inflated.

With reference to FIG. 5a, the tubular organ 19 is shown in cross-section with the cuff 11 of the present invention surrounding approximately one-half of the circumference thereof. In this view, the expandable component 13 is shown as being deflated and with the tissue tubular lumen 20 in an open state, which it could be in an incontinent subject. If the tubular tissue represents a urethra, that would represent a patient with severe incontinence or a patient with a "stove pipe" urethra, as normally, the urethra is devoid of an open lumen at rest. A lumen only exists when urine passes through it. The base member 12 of the cuff is held in intimate contact with the exterior wall of the tubular organ, e.g. the urethra, by means of the aforementioned hooks 27 and ultimately tissue ingrowth.

Figure 5B:
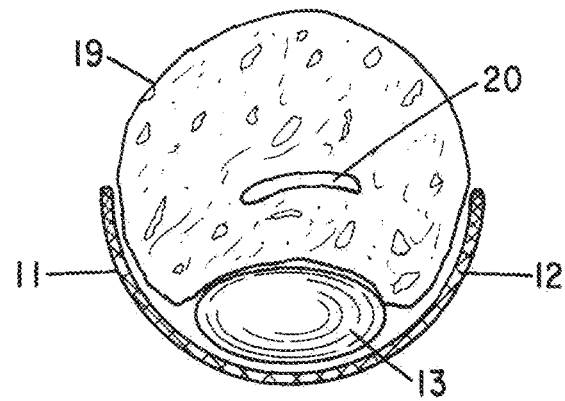
FIG. 5b shows the embodiment of the present invention coapted to a tubular organ and with the inflation component inflated.

FIG. 5b is a view like that of FIG. 5a, except with the expandable component 13 in its inflated state. As seen in this figure, the expandable component 13 pushes itself against the tubular wall to narrow or close the lumen 20 and at least increasing the resistance to fluid or other material flow therethrough.

In accordance with the present invention, by controlling the extent of inflation of the expandable component by either injecting an inflation fluid into a flaccid balloon or withdrawing fluid from a turgid balloon, the degree of closure and, hence, the resistance to fluid flow therethrough can be adjusted to the point where the tubular sphincter is capable of fully collapsing the tubular lumen and thereby keeps the subject in a dry condition such as in the case of an incontinent patient.

Those skilled in the art appreciate that the tubular organ urethra is normally without an open lumen. A lumen only exists when urine is passing through it. This means that the musculature of the urethral wall, including the sphincter muscles, are normally contracted to the keep the lumen closed, thereby preventing unwanted passage of urine, i.e., incontinence. This musculature relaxes during normal micturition. The brain sends signals to the muscles of the bladder wall, the deturusor muscle, to contract and, at the same time, to the sphincter muscles, including those muscles of the urethral wall to relax. In this way, urine is forced out of the bladder and flows down the (now relaxed) urethral tube and exits the body.

Since muscles and tissues consist of mostly water, their volume is essentially not compressible. The closed urethral tube, made of tissue, can be measured to have a certain diameter. As urine creates a passageway down this tube, the diameter of this passageway, because of the non-compressible tissue mass, will be translated into an increased circumference of the urethra, exhibiting an overall increased diameter and a thinner wall. Another way to express this is that the urethral wall will be stretched to accommodate this passageway created by the urine.

The urethral wall, containing the contracted muscle, can be compared to a circular rubber band. The urine, in creating the passageway, represents a force stretching the rubber band. As an example, if the diameter of the urine passageway translates to 5 mm, this 5 mm would, therefore, be distributed into the entire cross-section of the urethra. Each segment of the urethral wall and its muscles will be stretched an apportioned length for an aggregate total of 5 mm. If one were to artificially create a situation where the cross-sectional half of the urethral wall is restricted from becoming stretched, then the other half will have to be stretched twice as much to allow the same amount of the total required expansion of 5 mm.

The contracted musculature is analogous to that of a rubber band. Stretching will require a force. If a 15 mm long rubber band is stretched to be 20 mm long, a certain amount of force will be needed. If only half of the 15 mm rubber band is allowed to stretch, then the amount of force to stretch the 5 additional millimeters will be greater with the 7.5 mm rubber band. Similarly, a partially restricted urethral wall will require a greater force to open than if the urethral wall were not partially surrounded by the cuff. It is this added force that is required to stretch a shortened band that can be used in connection with one or more embodiments of the present invention. If a portion of such a urethra, esophagus or other organ is restricted from stretching or expanding, then it will take more force to stretch the remainder of the organ to achieve the same opening size.

Stiffness of material used, such as for a base member as characterized herein, can impart control and augment organ function. For instance, a stiffer base member can impart greater resistance against organ expansion. Accordingly, stiffness, as relative to both material used and the structural arrangement thereof, can be set or tuned to provide a desired resistance.

As shown in FIGS. 5a, 5b, 6a and 6b, the entire cuff 11 is in contact with the urethra and restricts only a portion of the urethral wall from stretching. The unrestricted portion can still be stretched, albeit requiring more force to do so. In stress urinary incontinence, urine is forced down the urethra as the bladder is being suddenly compressed by abdominal muscle during coughing, laughing and other common daily activities. In these patients, the urethral musculature is insufficient to maintain closure, such that it lets some urine to pass through during this sudden increase in pressure on the bladder. The amount of leakage varies from patient to patient, paralleling the degree of weakness of the musculature. Analogous situations occur in fecal incontinent and acid reflux.

During normal micturition, the urethral musculature relaxes and the urethral lumen will open to allow the passage of urine freely down the path. The harder the bladder squeezes, the more urine will rush out of the bladder and down the urethra, thus a faster flow rate. This faster flow rate translates to a thicker urine stream, reflecting a wider urethral lumen.

If a restriction were to be put completely around the urethra, such that none of the urethral wall under the restriction is allowed to be stretched, then no passage lumen can be created in the urethra and no urine can flow through it. This is somewhat analogous to males with a severe case of benign prostatic hyperplasia (BPH) in that the enlarged prostate gland impinges on the urethra and the patient is in retention, or unable to void.

In accordance with various embodiments, applying a partial restriction to stretching or expansion of the urethra results in an increased resistance to flow that will benefit most of the stress urinary incontinent patients, and yet when these patients want to void, the unrestricted portion of the urethral wall can relax automatically, via normal and natural neural signaling, allowing urine to flow through as any normal micturition. Such an approach can be implemented with acid reflux and fecal incontinence situations, and in other situations in which controlled expansion and flow of material is desired for a biological structure (e.g., tube).

Figure 7A:
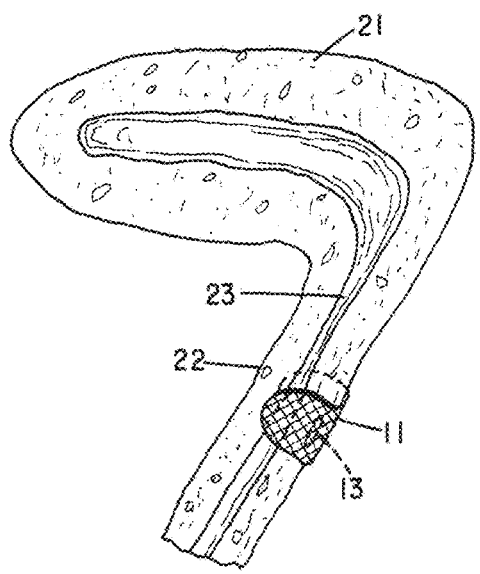
FIG. 7a shows the cuff of the present invention disposed on a tubular urethra proximate the bladder neck and with the expandable component deflated.
Figure 7B:
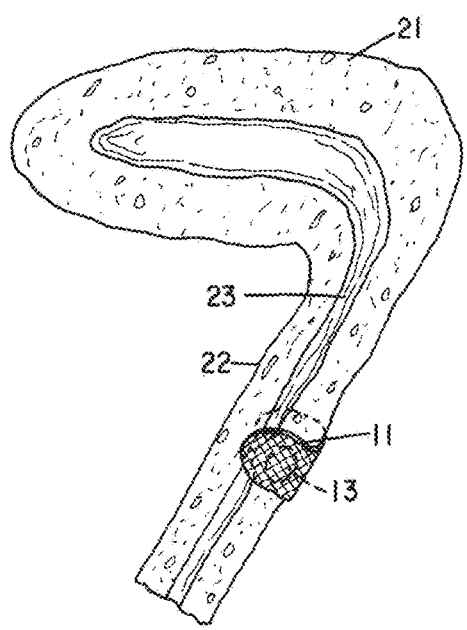
FIG. 7b is a view like that of FIG. 7a but with the expandable component inflated.

FIG. 7a is a sagittal view taken laterally through the bladder, bladder neck and urethra of a woman. Here, the partial cuff 11 is adhered to the urethra at a location proximal to the external urinary sphincter. Again, the entire cuff 11 is shown as only partially surrounding the urethra 22 and when the inflatable component 13 is in its deflated condition (FIG. 7a), the lumen 23 is unrestricted. By injecting a suitable inflation fluid into the interior of the expandable component or balloon 13, the urethral wall is displaced in a direction to at least partially occlude and increase the resistance to flow of the lumen 23. In accordance with the invention, however, the expandable component 13 is only expanded to the point where, at rest, urine flow through the urethra is blocked. However, when the signals from the brain result in contraction of the bladder wall, the resulting increase in fluid pressure will allow the relaxed urethra muscles to expand sufficiently so that the lumen will open and normal voiding may take place.

In order to apply the cuff of the present invention to the urethral wall, a special tool shown in FIG. 8a may be used. It is seen to comprise a pair of handles 24 having opposed jaws 25 on one end thereof and where a hinge pin or rivet 28 allows the jaws to open and close relative to one another upon appropriate manipulation of the handles 24. The jaws include a plurality of raised projections, as at 26, that are designed to cooperate with the hooks 27 on the flexible base member of the cuffs 11 to cause them to impinge into the outer urethral wall when the jaws are made to close relative to one another about the tubular organ being addressed.

FIG. 8b illustrates the tool of FIG. 8a with a cuff of the present invention positioned between the jaws 25 of the tool just prior to use. The optional expandable component or balloon 13 is centrally disposed. The surgeon will align the index mark or guide line 14 with a length of the urethra as shown in FIG. 8c, and now, when the handles are squeezed together, the jaws 25 will close with the urethra cradled therein. See FIG. 8d. The projections 26 on the tool jaws are designed to cooperate with the hooks on the base member 12 to thereby cause the hooks to pierce into the urethral wall as shown in FIG. 8e and thereby hold the cuff in partially surrounding relation relative to the circumference of the urethra. After a period of time, measured typically in weeks, tissue ingrowth and fibrosis will have occurred, thereby embedding the cuff 11 into the urethral wall and restricting expansion of the urethral wall in the zone occupied by the cuff. As earlier described, this increases the flow resistance of the urethra without totally causing occlusion and thereby allowing normal micturition while inhibiting unwanted urine flow from the increases in bladder pressure due to laughing, sneezing, coughing, etc.

In accordance with another aspect of the invention, the cuff may comprise a flexible base member having an expandable component affixed to one major surface of the base member. The cuff will increase the urethral resistance of urine flow by creating a direct and adjustable coaptation in the urethra, but not occluding it. The expandable component is situated on one side of the urethra between the urethral wall and the cuffs base member. As the expandable component inflates, it forces the urethral wall inward as the other side of the expandable member is confined by the cuffs inelastic base member. This results in an inward indentation of the urethral wall, resulting in narrowing of the urethral lumen, leading to an increased coaptation and resistance to urine flow and decreased incontinence.

As the entire cuff is attached only to the urethra and not extending to surrounding anatomical structures, the pressure produced by the expandable component will remain the same regardless of the urethral movements. This is a critical, non-obvious difference between the present invention and the traditional urinary bladder support slings. Also, because the entire cuff is attached only to the urethra, the amount of coaptation can be adjusted, tailoring to the need of the patient's incontinence condition.

In various embodiments, a cuff as characterized herein will not constrain the segment of the urethra opposite the cuff from relaxation and expanding during normal urination, and urine can, therefore, flow naturally past the cuffed region. The patient does not have to actively manipulate a pump mechanism to open the urethral lumen for micturition to occur. Therefore, patients will be able to micturate normally and naturally without any added manipulation.

Though various embodiments can be used for women, as incontinence is more pervasive in women, it is also applicable for men's incontinence condition, such as may result in post-prostatectomy situations and in certain post transurethral resection of the prostate situations.

In certain instances, the expandable component on the base member does not need to be expanded, as the act of surgery and its resultant scar formation would provide sufficient augmentation to the urethra to achieve continence.

Some embodiments involve a cuff that only partially surrounds the urethra or other tubular organ through which flow is to be resisted. Other embodiments involve a cuff composed of a base member and an expandable component on the base member. A portion of the base member can be firmer than the rest of the base member. The partial cuff is adapted to be attached to the urethra with the expandable component facing the urethra.

The expandable component is implemented as an inflatable, expansible balloon, in accordance with one or more embodiments. The inflation and deflation of the balloon can be done through a port, such as a tube, that can be permanently attached to or detachable from the balloon. The other end of the tube may have a self-sealable end for injection or withdrawal of the inflation material during the adjustment of the size of the balloon suitable for the patient's condition. The inflation port may also be a self-sealing patch on the cuff. This patch can be felt through the skin or seen noninvasively via other means for convenient identification by the physician doing the balloon sizing. The self-sealing material of the patch permits piercing by an injection needle without leaking when the needle is removed.

The fixation of the device to the urethra is accomplished by first fastening the base member to the urethral wall and/or biological tissue, followed by tissue ingrowths into the material of the base member over several weeks postsurgery.

In some embodiments, the base member material includes a biocompatible lattice-like member having fringes extending at least beyond the two ends of the balloon and these fringes provide easy stitching or fastening to the urethra by the surgeons and the lattice will allow tissue ingrowths to further naturally and firmly secure the attachment of the cuff to the wall of the involved tubular organ.

The lattice-like fringe can extend along the entire perimeter of the cuff. The fringe area can be substantially larger than the expandable component. A flattened shape of the cuff may be rectangular, or trapezoidal, but with rounded ends.

The fastening of the cuff to the tubular organ can be accomplished by sutures or by small hook-like elements placed on the cuff or by a suitable adhesive, such as tissue glue, albumin and glutaraldehyde tissue adhesives or polyethylene glycol polymers. The hook-like elements are placed on the same side of the cuff as the expandable component. These hook-like elements fasten the base material to the wall tissue of the anatomical tube, such as the urethral wall tissue, to hold the cuff in place while tissue in growths is taking place. Once tissue ingrowths is complete, the cuff becomes integrated into the wall of the tubular organ and these hook elements will no longer be necessary. They can dissolve and be absorbed by the body.

The hook-like elements can be pre-affixed onto the base member of the cuff or applied by the surgeon at the time of implant.

As a further feature, a combination of two types of hook-like elements can be utilized as fasteners. The pre-affixed hook-like elements on the base member serve as a fast general attachment of the cuff and then supplemented by placement of additional hook-like elements to refine the cuff attachment to the tissue. Tissue glue or tissue adhesive may also be used to supplement the hook-like elements.

The hook-like elements can be made of a biocompatible and bioresorbable or degradable material known in the art. The hook-like elements eliminate the need for surgeons to suture the cuff to the urethra. With these hooks, the cuff may be applied to the urethra with a simple tool. For example, a forceps-like tool can be used to apply the cuff to the urethra. Its jaws can be suitably shaped to accommodate the curvature of the tubular organ.

The hooks can be pre-assembled onto the cuff. As already described in connection with FIGS. 8a-8e, two curved forceps jaws, each capturing an end of the cuff, can be used to push the cuff towards and place it against the tubular organ, e.g., the urethra, to partially surround it. Once in place, the handles of the tool are manipulated to set the hooks on the cuff into the wall of the tubular organ from outside in.

The tool embodies a means to hold onto the cuff before deployment of the cuff onto the tissue. Once the cuff is in place and its hooks are embedded into the tissue, the tool can be withdrawn, releasing the cuff and leaving it attached to the tissue.

The means employed to cause the tool's jaws to hold onto the cuff may be small pin-like or hook-like protrusions 26 disposed at an angle on the inside curves of the jaws. These protrusions prevent the cuff 12 from falling off while it is being pushed forward along and against the wall of the tubular organ, as the action of pushing forward forces the cuff to be tightly engaged to the forward pointing protrusions 26. However, after the cuff is fastened onto the tissue wall of the tube, by pulling back the tool, it releases the cuff 12 as these protrusions are now pointing rearward as compared to the movement of the tool jaws. Similarly, but with an opposite intent, the hook-like elements 27 on the cuff will have the hooks pointing rearwards as the cuff is pushed forward by the tool, so that once they are engaged into the tissue, the hook-like elements prevent the cuff from sliding back and off of the tubular organ, e.g. a urethra.

Figure 9:
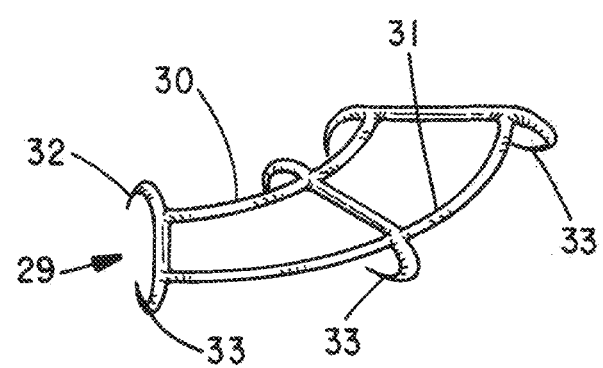
FIG. 9 illustrates an attachment hook assembly.
Figure 10:
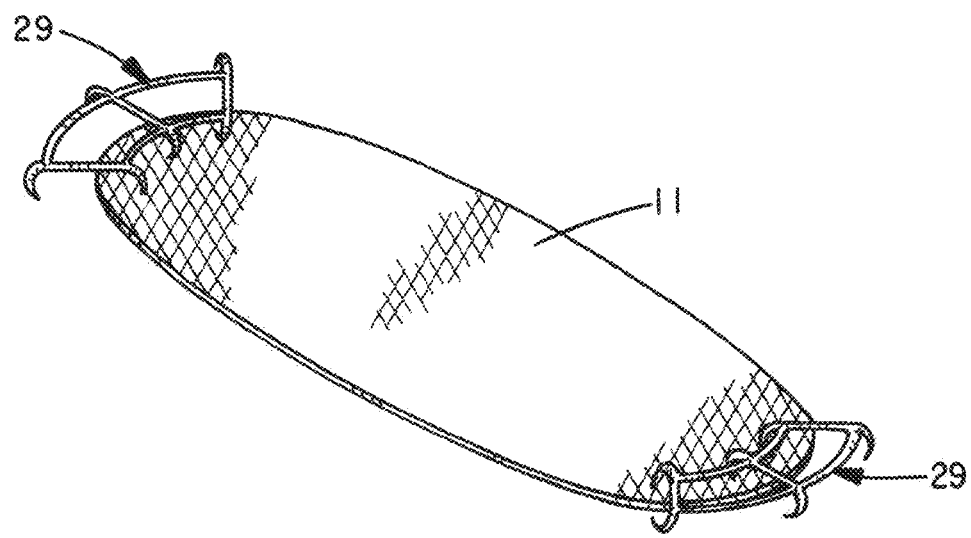
FIG. 10 illustrates the hook assembly of FIG. 9 affixed to a cuff member.

Among different ways of having the hooks preassembled onto the cuff, as in FIG. 3b, an embodiment of a hook assembly like that shown in FIG. 9 may be utilized in a manner illustrated in FIG. 10. FIG. 9 illustrates an example of a hook assembly 29 to be used for attachment of the cuffs base member to the exterior wall surface of a biological tube. The hook assembly may consist of a plurality of hooks 32 that are joined by a pair of connectors 30 and 31 where hooks 32 serve to engage the tissue of the biological tube and the hooks 333 serve to engage the base member 12 of the cuff 11. The connectors 30 and 31 serve to space the hooks in desired locations on the cuff and provide even tension for maintaining the shape of the cuff during attachment to the biological tube. The connectors 30 and 31 can also provide an easy way for reversibly engaging and disengaging the deployment tool. Furthermore, the location of the connector 30 can be situated in a position proximate to the hooks 32 such that it will assist in the deployment handle of the tool pushing down on the hooks 32 in engaging the tissue of the biological tube. Different hook numbers and connectors on the hook assembly can be applied to fit the needs of the particular cuff application. For larger cuffs, one or more of sets of the hooks can be utilized. FIG. 10 illustrates one possible 10 placement of the hook assemblies 29 on the opposed ends of the cuff 11.

The expandable component on the partial cuff can be inflated precisely to achieve the degree of urine flow resistance desired. This is feasible as the adjustment can be carried out a few weeks after the surgery at a time when tissues have healed and inflammation has subsided, therefore allowing more meaningful and accurate adjustment of the urethral coaptation.

As already indicated, the expandable component can be an inflatable balloon with different shape configurations. The expandable component can have different forms, e.g., it could be a single balloon as in FIG. 1, a set of two or more narrow balloons as in FIG. 2, resembling ridges, on the base member. These ridges can be applied to the urethra such that they extend across the urethra, perpendicular to the urine flow pathway. These ridges can also be applied to the urethra such that they are in line with the urethra, parallel to the urine flow pathway creating a longer compression zone. These ridges can also be bilateral on opposite sides of the urethra.

In accordance with a further embodiment, the ridges can also be preformed so that no inflation would be needed. The preformed ridges can be made of silicone rubber or other biocompatible material and there can be open spaces between the pair of ridges.

The material of the base member as well as the inflatable balloon may be made of flexible, biocompatible material, such as silicone rubber. The base member can be made of polypropylene or polyethylene strands or latticed structures similar to those used in hernia repairs of general surgery and slings of urological surgery.

Additional mechanisms, such as ports and tubes, can be added to make the expandable component of the cuff inflatable and deflatable for future adjustments as the patient's condition changes. The inflation and deflation port can be placed in locations that it can be used in the future without surgery.

Rather than comprising a balloon, the expandable member may comprise a small pouch of moisture permeable material, such as a silicon rubber membrane, micro-porous Teflon membrane or a regenerated cellulose membrane, where the pouch contains a hydrophilic material, such as agarose particles, polyacrylamide particles or serum albumin and that expands on the absorption of moisture.

A midline marking 14 can be applied to the bottom of the base member to assist the surgeon in aligning the device over the urethra or other tubular organs. Surgically, the cuff can be implanted trans-vaginally, via a single midline incision or a flap at the anterior wall of the vagina in incontinent women patients. To make the surgery easier and as earlier presented, the cuff can be deployed by a deployment tool that holds the cuff for attachment to the outside of the tubular organ and releases the cuff after the cuff is engaged into the tissue.

In a still further alternative embodiment, the cuff may comprise a C-shaped clip formed from a resilient medical-grade plastic or a biocompatible metal rather than a synthetic mesh and that is designed to partially surround a tubular organ, e.g., the urethra. The clip may be designed to span an arc greater than 180° but less than 360°, or in a range from about 220° to 300° and the effective diameter of which creates somewhat of an interference fit with the tubular organ that is made to surround.

Figure 11:
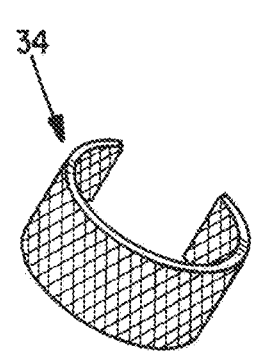
FIG. 11 illustrates a further embodiment.
Figure 12:
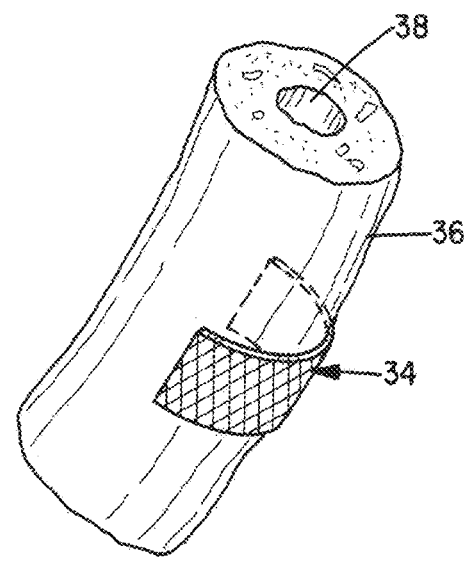
FIG. 12 shows the further embodiment of FIG. 11 affixed to a tubular organ.

Referring to FIG. 11, a first type of C-clip is illustrated and identified by reference numeral 34. FIG. 12 shows the C-clip 34 when clamped onto a tubular organ 36. The presence of the C-clip prevents expansion of the tubular organ 36 subtended by the clip and, in accordance with the present invention, increases the resistance to flow through the lumen 38 of the tubular organ.

While the C-clip shown in FIGS. 11 and 12 comprise a continuous metal or plastic arcuate strip, the clip may also be fenestrated, such as by laser cutting, to facilitate tissue ingrowth and fibrosis therethrough and integration with the vessel wall.

Figure 13:
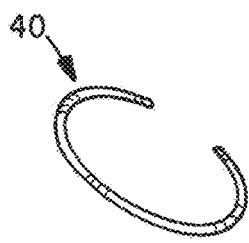
FIG. 13 is yet another embodiment.
Figure 14:
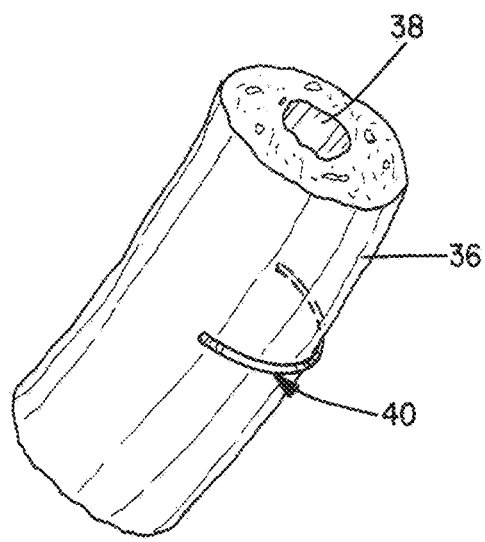
FIG. 14 shows the embodiment of FIG. 13 affixed to a tubular organ.

FIG. 13 shows a C-band 40 comprising a metal or plastic wire or strand that exhibits resiliency, allowing it to be spread for placement about a tubular organ, but when released, closes about the tubular organ as shown in FIG. 14. Rather than simply using a single C-band 40, plural such bands may be placed separately or joined about the tubular organ in a closely spaced relationship so as to create a desired degree of augmentation on the tubular organ and, therefore, greater resistance to flow through the lumen 38 thereof. It is also contemplated that one or more C-bands 40 can be applied over a soft, partial cuff like that shown in FIG. 1*b* to hold it in place on the tubular organ while tissue ingrowth occurs. When so used, the C-bands can be made of bio-resorbable or bio-degradable material.

FIG. 15 shows yet another way of implementing the partial banding of a fluid carrying tubular organ to increase its resistance to flow. Here, a polypropylene mesh strip 42 or other fenestrated structure is supported by a frame member 44 formed from a suitable metal or plastic exhibiting a memory property when stressed below its elastic limit and then released. Without limitation, the frame may comprise a nitinol wire that has been heat treated in a mold to form the C-shape configuration illustrated in FIG. 15. When the band is spread, placed about a tubular organ and then released, the mesh strip is brought into intimate engagement with the tubular organ and over a few-week period becomes integrated or fibrosed onto the tubular wall, thus reinforcing the organ wall at the placement site.

The cuff is suitable for treating females with stress incontinence. The cuff is also suitable for men with incontinence, such as may occur after radical prostatectomy, other procedures or in conditions where an increased resistance to urine flow would be beneficial in controlling incontinence.

The cuff of the present invention may find other uses. It can be suitable to treat ureteral reflux or to minimize food regurgitation or reflux into the esophagus, limit the food intake into the stomach, and strengthen the ventricular wall of the hypertrophied heart and blood vessels. It is also contemplated that the partial cuff of the present invention can be used to minimize fecal incontinence. In fact, the partial cuff may be suitable for treating conditions where material is passed in an anatomical tube in which the flow of material needs to be modulated.

Depending on the clinical condition it is being used for, the strength or the stiffness of the cuffs as characterized herein can be designed to fit specific applications. For example, in the case of treating acid reflux, the cuff can be made entirely of nitinol material fashioned with a latticed or cross-struts configuration or having just parallel struts. The number of struts and the thickness of nitinol material used will determine the stiffness of the device. For example, for acid reflux or GERD, the normal lower esophageal sphincter pressure is approximately 20±10 mmHg, a cuff can be designed with stiffness that will require 20 mmHg pressure to push open. While more the ends are being pushed open, the higher the pressure will be required, analogous to the natural sphincter action. In the example of a cuff being used to augment anal sphincter for fecal incontinence control, the stiffness can be more, as more pressure will be required, while for stress urinary incontinence use, the stiffness can be less.

In various embodiments, a cuff is shaped to allow preferential passage of material through the biological tube in one direction but hinders its reverse flow such as in treating acid reflux. In acid reflux or gastroesophageal reflux disease (GERD), acidic stomach contents reflux into the esophagus causing burning and discomfort to the sufferer. Over time, erosion of the esophageal lining occurs and could cause a condition known as Barrett's Esophagus which increases the probability of it becoming esophageal cancer.

Figures 16A, 16B, 16C:
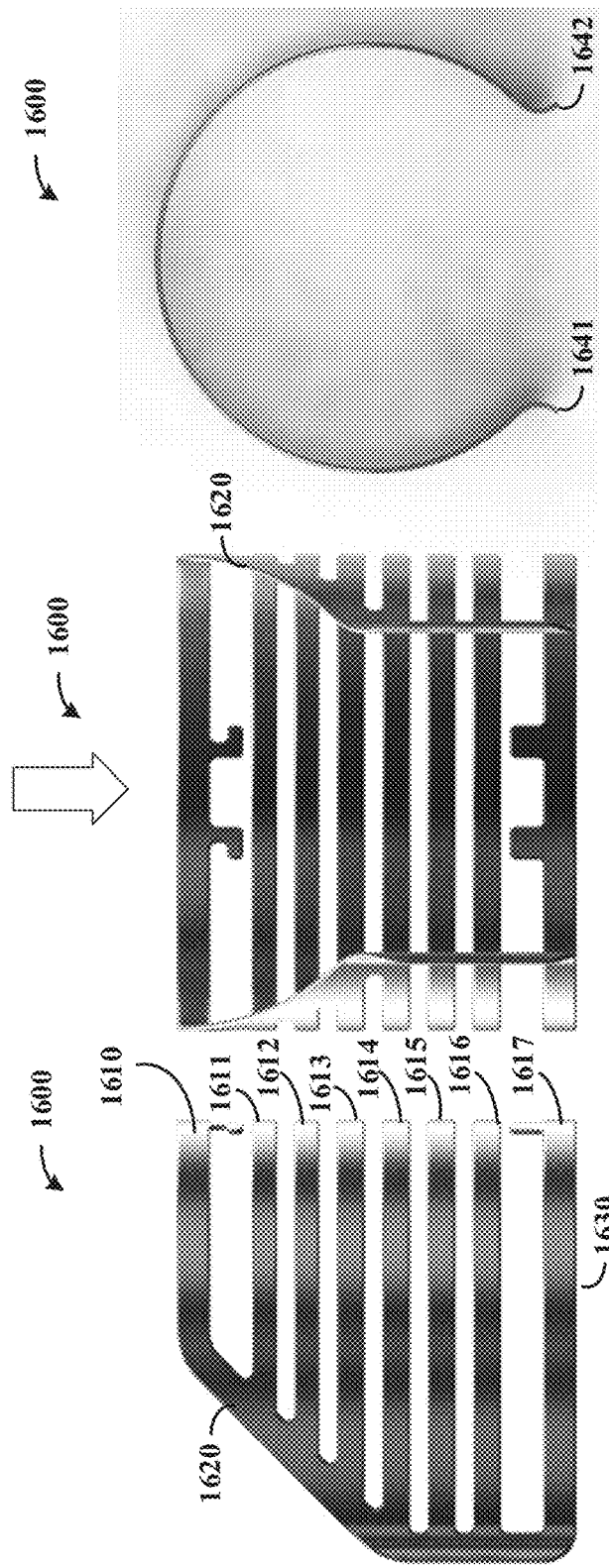
FIGS. 16a-16c show side, front and top views, respectively, of an apparatus in accordance with one or more embodiments.

FIGS. 16*a*-16*c* show side, front and top views, respectively, of an apparatus 1600 in accordance with one or more embodiments. The apparatus 1600 includes a plurality of supporting structures 1610-1617 aligned as shown from a tapered upper portion 1620 of the apparatus to a blunt end 1630. As shown in the top view of FIG. 16*c*, the apparatus 1600 is shaped to partially encircle a tube. Tapered portion 1620 may facilitate coupling of the apparatus around the tube and/or directional flow control.

In some embodiments, and referring to FIG. 16*b*, passage of material in the direction shown by the arrows is facilitated by the tapered portion 1620, providing an effectively larger opening via which flow of material may be achieved. Reverse flow, in a direction opposite the arrows, can be mitigated via the blunt end 1630 of the apparatus, which provides a relatively smaller opening via which material may flow within a tubular structure partially encircled by the apparatus. Such embodiments, may be implemented, for example, to treat acid reflux type situations as discussed above, with the apparatus 1600 being applied around an esophagus. For instance, food bolus entering the apparatus from above as shown in FIG. 16*b* may form a wedge-shaped esophageal tube enlargement, which facilitates opening/deformation of the apparatus 1600 and allows passage of the food bolus through the apparatus. However, under conditions in which food bolus or other material may be pushed up through the esophagus from below in a reverse-flow scenario, the blunt lower end 1630 provides greater resistance to expansion, and thus can prevent such flow.

Various embodiments include a design feature of having sloped leading edges, such as shown in FIGS. 16*a-c*, which allow a biological tube to be less constrained at that end of the device. This represents a larger opening at that end of the device. In the GERD example, as the food bolus is coursing down the esophagus propelled by the peristaltic action of the esophagus, it would expand the esophagus diameter by expanding the normally closed lumen of the esophagus. A cuff can be implemented to constrain this esophageal wall expansion. However, with the slope edges towards the incoming food bolus, that segment of the esophagus will be less constrained at the beginning of the device, therefore allowing that portion of the esophagus to be expanded easier. The food bolus entering the device zone would thus form a wedge shaped esophageal tube enlargement. This wedge effect facilitates an easier expansion of, or an easier pushing open the cuff to allow passage of the food bolus. In the reverse direction, when the acidic stomach content is being forced upward, it immediately faces the blunt ends of the cuff, without a wedge effect taking place. The full force of the device is thus immediately imparted on the reverse flow to hinder acid reflux.

One or more cuffs as characterized herein have a wrap angle greater than 180 degrees which results in a device with a lateral opening smaller than the diameter of the device. This will prevent the device from falling off the tubular organ, but will also hamper the device from being easily pushed onto the biological tube without it first being pulled open. The sloped edges create a larger device opening such that the device can be easily pushed onto the biological tube that has a diameter equal to the device diameter without the necessity of the device being pulled open first, such as with a deployment tool illustrated in FIG. 8*a*-8*d*. This would simplify and facilitate surgical implantation of the cuff onto a biological tube, especially in a laparoscopic procedure.

Referring again to FIGS. 16*a*-16*c*, the apparatus 1600 can be implemented as follows. A perimeter structure extends around the apparatus and including structure at 1610 and extending along a tapered region at 1620 and to 1630 at a blunt end, contiguously around supporting struts 1611-1616. The apparatus 1600 can partially encircle a tubular organ, with the perimeter structure exhibiting a semi-cylindrical shape as depicted via the top view in FIG. 16*c*, extending contiguously from a first end at 1641 to a second end at 1642 along a circumference thereof, with a gap between the first and second ends along the circumference. The semi-cylindrical shape has a tapered edge at 1620/1610 and a blunt edge at 1630, respectively at opposing ends of the perimeter structure along the axis of the semi-cylindrical shape (with the axis running along the direction of the arrows in FIG. 16*b*). The tapered edge has a length along the circumference that is less than a length along the circumference at the blunt edge. The struts extend between respective portions of the perimeter structure with spaces between them that facilitate ingrowth of tissue of the tubular organ. When applied to a tubular organ, the struts and perimeter structure mitigate expansion of a first portion of a sidewall of the tubular organ to which the apparatus is coupled while allowing expansion of a second portion of the tubular organ between the first and second ends 1641/1642 along the circumference.

Figure 17C:
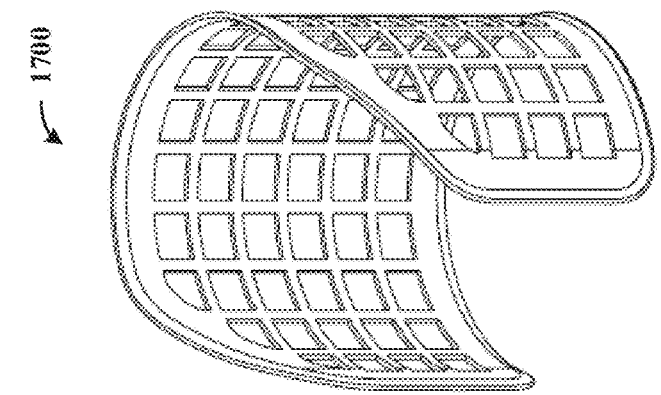
Figure 17B:
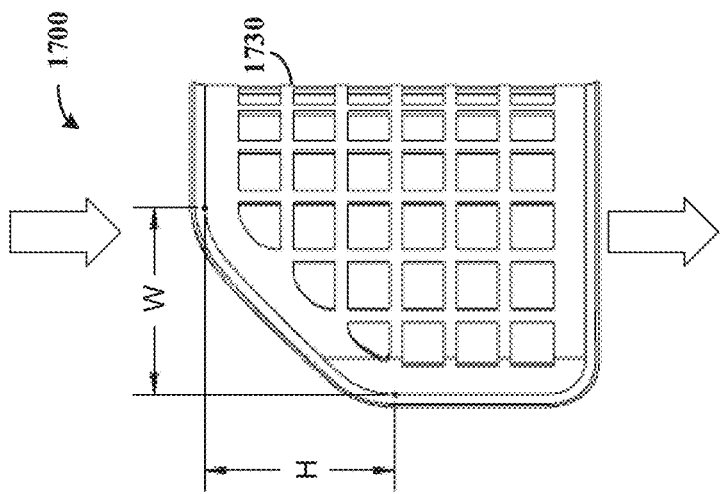
Figure 17A:
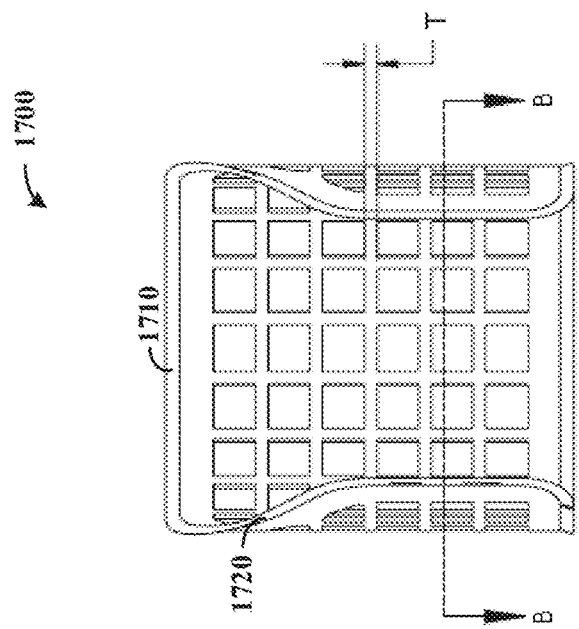
Figures 17D, 17E, 17F:
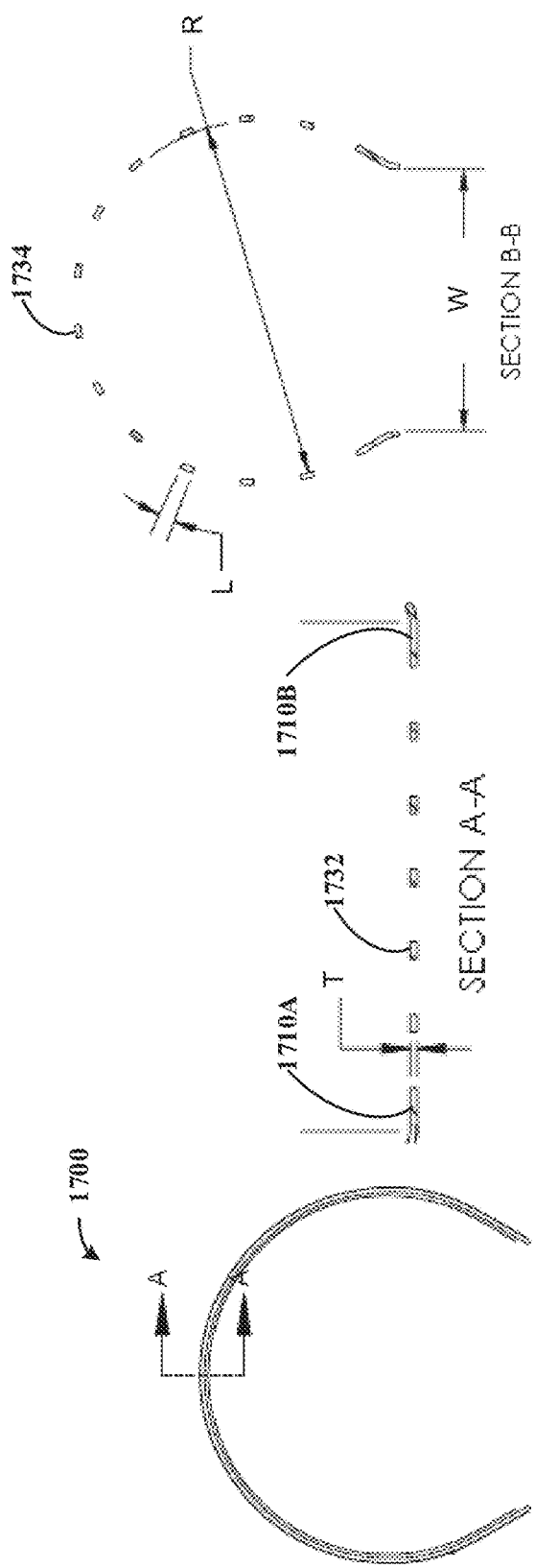

FIGS. 17*a*-17*f* show respective views of a latticed structure 1700 (e.g., cuff), in accordance with another embodiment. FIGS. 17*a* and 17*b* respectively show front and side views, with FIGS. 17*c* and 17*d* showing perspective and top views. The structure 1700 includes a perimeter structure 1710 having a tapered region at 1720, with a lattice structure 1730 connected within the perimeter. By way of example, the lattice structure is shown in FIG. 17*a* as having lattices with a thickness T, and the tapered region 1720 is shown in FIG. 17*b* as having a height H and width W, that can be adjusted to achieve a desired taper and resistance to flow. The tapered region 1720 facilitates flow in the direction as shown by arrows in FIG. 17*b*.

FIG. 17*e* shows section A-A from FIG. 17*d*, with perimeter components at 1710A and 1710B, and multiple horizontal lattice portions including lattice portion 1732. The perimeter structure and lattices are shown with a common thickness T. However, the thickness and distance between lattices can be varied to control resistance to flow.

FIG. 17*f* shows section B-B from FIG. 17*a*, showing an effective top section view with multiple vertical lattice portions including lattice portion 1734 shown by way of example. The length L of each lattice portion can be set to achieve desired resistance to flow. Similarly the radius R of the structure 1700 and width W of an open end thereof can also be set to a particular application, as may be dictated by a type of organ to which the apparatus is to be applied and/or variations in size (e.g., as may relate to male, female, youth and other size-related differences).

Figure 18:
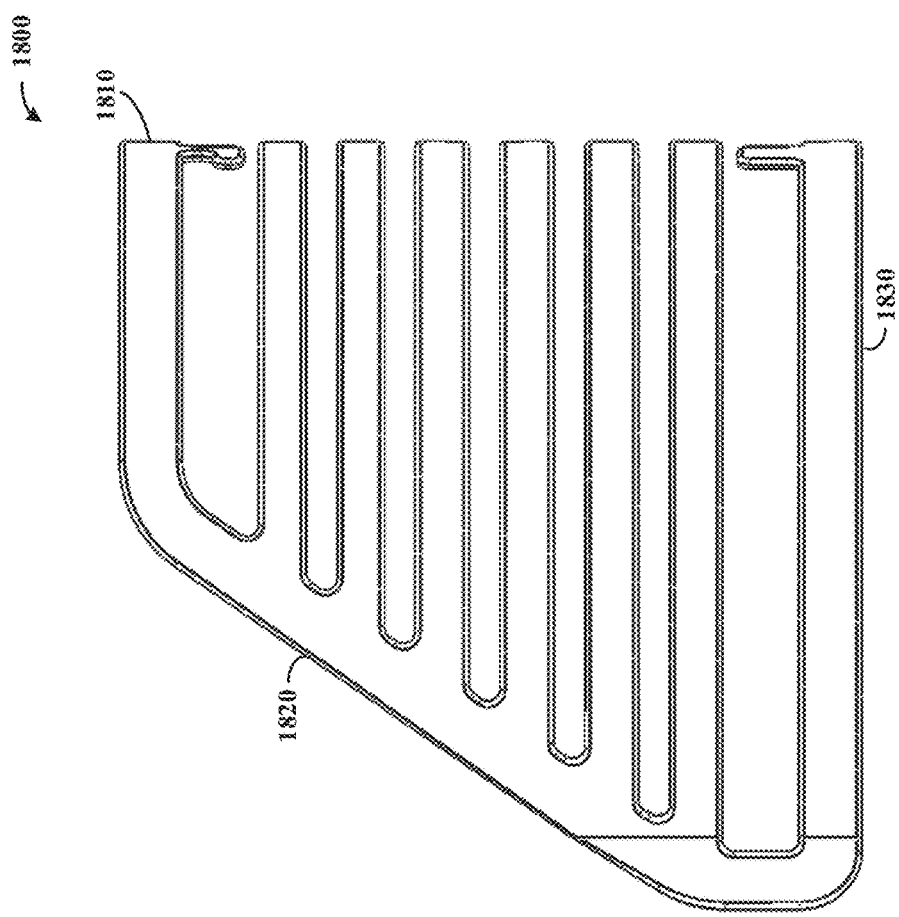
FIG. 18 shows an apparatus, similar to that in FIGS. 16a-16c, with a steeper sloped taper edge, in accordance with another embodiment.

FIG. 18 shows an apparatus 1800, similar to apparatus 1600 in FIGS. 16*a*-16*c*, with a steeper sloped taper edge, in accordance with another embodiment. The apparatus 1800 includes a perimeter structure 1810 having a tapered end region 1820 and a blunt end region 1830. The slope of the tapered end region 1820 is high relative, for example, to that of apparatus 1600. This higher slope facilitates more sidewall movement/flexibility of a tubular organ to which the apparatus is attached, and therein a greater amenability to flow.

Based upon the above discussion and illustrations, those skilled in the art will readily recognize that various modifications and changes may be made to the various embodiments without strictly following the exemplary embodiments and applications illustrated and described herein. For example, different length cuffs can be implemented to suit particular applications, such as to provide fluid flow restriction tailored to a particular application and/or patient. In addition, the various embodiments described herein may be combined in certain embodiments, and various aspects of individual embodiments may be implemented as separate embodiments. Such modifications do not depart from the true spirit and scope of various aspects of the invention, including aspects set forth in the claims.

What is claimed is:

1. An apparatus comprising:
 a perimeter structure configured and arranged to partially encircle a tubular organ, the perimeter structure exhibiting a semi-cylindrical shape extending contiguously from a first end to a second end along a circumference thereof with a gap between the first and second ends along the circumference, the semi-cylindrical shape having a tapered edge and a blunt edge respectively located at opposing ends of the perimeter structure along an axis of the semi-cylindrical shape, the tapered edge having a length along the circumference that is less than a length along the circumference at the blunt edge; and
  a plurality of struts extending between respective portions of the perimeter structure with spaces between the struts that facilitate ingrowth of tissue of the tubular organ, the plurality of struts being configured and arranged with the perimeter structure to mitigate expansion of a first portion of a sidewall of the tubular organ to which the apparatus is coupled while allowing expansion of a second portion of the tubular organ between the first and second ends along the circumference.

2. The apparatus of claim 1, wherein the blunt edge is configured and arranged to exhibit a resistance to flow of material through the tubular organ entering from the blunt edge that is greater than a resistance to flow of material through the tubular organ entering from the tapered edge.

3. The apparatus of claim 1, wherein the perimeter structure and plurality of struts are configured and arranged to mitigate the expansion of the first portion of the tubular organ of a patient while connected to the tubular organ and without connection to other biological structure in the patient's body in which the tubular organ resides.

4. The apparatus of claim 1, wherein the perimeter structure and plurality of struts are configured and arranged with a structural rigidity between the first and second ends that is sufficient to independently limit flow of material through the tubular organ with the entire apparatus connected to the sidewall.

5. The apparatus of claim 1, wherein the blunt edge is configured and arranged to exhibit a rigidity that is greater than a rigidity exhibited by the tapered edge, therein providing a resistance to flow of material through the tubular organ entering from the tapered edge that is less than a resistance to flow of material through the tubular organ entering from the blunt edge.

6. The apparatus of claim 1, wherein the tubular organ resides in a patient having a stomach, and the perimeter structure is configured and arranged with the plurality of struts to treat acid reflux by, when coupled partially around a patient's esophagus with the tapered edge at an upper end of the perimeter structure and the blunt edge at a lower end of the perimeter structure, facilitate passage of food down through the esophagus and entering the perimeter structure via the tapered edge and into the patient's stomach, and to mitigate the passage of material up through the esophagus and entering the perimeter structure via the blunt edge.

7. The apparatus of claim 1, wherein the perimeter structure and plurality of struts are configured and arranged to:
  provide a relatively large opening for material flowing through the apparatus from the tapered edge, relative to an opening at the blunt edge; and
  form a wedge of material extending into the semi-cylindrical shape that facilitates the flow of the material through the apparatus.

8. The apparatus of claim 7, wherein the perimeter structure and plurality of struts are configured and arranged to facilitate the formation of the wedge of material and to utilize the wedge of material to deform the perimeter structure and facilitate flow of the material through the semi-cylindrical shape.

9. The apparatus of claim 1, wherein the perimeter structure has at least two tapered regions at the tapered edge.

10. The apparatus of claim 1, wherein the plurality of struts are arranged in a lattice structure.

11. The apparatus of claim 1, wherein
  the tapered edge is configured and arranged to extend around a majority of a circumference of the tubular organ and perpendicular to flow of fluid through the tubular organ, and
  the blunt edge is offset from the tapered edge by a length of the apparatus that extends along the length of the tubular organ, and is configured and arranged to extend around a majority of the circumference of the tubular organ and perpendicular to flow of fluid through the tubular organ.

12. A method comprising:
  coupling an apparatus having a perimeter structure and a plurality of struts extending between respective portions of the perimeter structure to partially encircle a tubular organ, in which:
    the perimeter structure exhibits a semi-cylindrical shape extending contiguously from a first end to a second end along a circumference thereof with a gap between the first and second ends along the circumference, the semi-cylindrical shape having a tapered edge and a blunt edge respectively located at opposing ends of the perimeter structure along an axis of the semi-cylindrical shape, the tapered edge having a length along the circumference that is less than a length along the circumference at the blunt edge, and
    the plurality of struts are arranged with spaces therebetween that facilitate ingrowth of tissue of the tubular organ; and
  using the plurality of struts with the perimeter structure to mitigate expansion of a first portion of a sidewall of the tubular organ to which the apparatus is coupled while allowing expansion of a second portion of the tubular organ between the first and second ends along the circumference.

13. The method of claim 12, further including utilizing the blunt edge to exhibit a resistance to flow of material through the tubular organ entering from the blunt edge that is greater than a resistance to flow of material through the tubular organ entering from the tapered edge.

14. The method of claim 12, wherein using the plurality of struts with the perimeter structure to mitigate the expansion of the first portion of the sidewall includes mitigating the expansion without coupling the apparatus to other biological structure in a patient's body in which the tubular organ resides.

15. The method of claim 12, wherein coupling the apparatus includes coupling the perimeter structure and plurality of struts with a structural rigidity between the first and second ends that is sufficient to independently limit flow of material through the tubular organ with the entire apparatus connected to the sidewall.

16. The method of claim 12, further including using the plurality of struts with the perimeter structure to provide a resistance to flow of material through the tubular organ entering from the tapered edge that is less than a resistance to flow of material through the tubular organ entering from the blunt edge.

17. The method of claim 12,
  wherein coupling the apparatus includes coupling the apparatus partially around a patient's esophagus with the tapered edge at an upper end of the perimeter structure and the blunt edge at a lower end of the perimeter structure;

wherein using the plurality of struts with the perimeter structure to mitigate the expansion of the first portion of the sidewall while allowing the expansion of the second portion of the tubular organ includes facilitating passage of food down through the esophagus and entering the perimeter structure via the tapered edge and into the patient's stomach; and further including treating acid reflux by mitigating the passage of material up through the esophagus and entering the perimeter structure via the blunt edge, by using the plurality of struts with the perimeter structure at the blunt edge to provide an increased resistance to flow of material through the perimeter structure entering via the blunt end, relative to resistance to the passage of the food entering the perimeter structure via the tapered edge.

18. The method of claim 12, further including using the plurality of struts with the perimeter structure a the tapered edge to provide a relatively large opening for material flowing through the apparatus from the tapered edge, relative to an opening at the blunt edge, to form a wedge of material extending into the semi-cylindrical shape, and to use the wedge of material to deform the perimeter structure and facilitate flow of the material through the semi-cylindrical shape.

19. The method of claim 12, wherein the tapered edge is configured and arranged to extend around a majority of a circumference of the tubular organ and perpendicular to flow of fluid through the tubular organ, the blunt edge is offset from the tapered edge by a length of the apparatus that extends along the length of the tubular organ, and is configured and arranged to extend around a majority of the circumference of the tubular organ and perpendicular to flow of fluid through the tubular organ, and allowing expansion of the second portion of the tubular organ between the first and second ends along the circumference includes allowing expansion of the second portion including a portion of the tubular organ along the tapered edge.

* * * * *